United States Patent [19] [11] Patent Number: 4,573,967
Hargrove et al. [45] Date of Patent: Mar. 4, 1986

[54] VACUUM VIAL INFUSION SYSTEM

[75] Inventors: William W. Hargrove, Indianapolis; Dale C. Harris, Fairland; Michael J. Akers, Greenwood, all of Ind.; Charles R. Sperry, Westport, Conn.

[73] Assignee: Eli Lilly and Company, Indianapolis, Ind.

[21] Appl. No.: 558,060

[22] Filed: Dec. 6, 1983

[51] Int. Cl.$^4$ .............................................. A61W 5/00
[52] U.S. Cl. ...................................... 604/56; 604/85; 604/92; 604/411
[58] Field of Search ............................. 604/56, 82–88, 604/92, 411–416; 426/404; 53/432

[56] References Cited

U.S. PATENT DOCUMENTS

| | | | |
|---|---|---|---|
| 2,863,779 | 12/1953 | Envoldsen | 426/404 |
| 3,001,525 | 10/1957 | Hendricks | 604/416 |
| 3,872,867 | 3/1975 | Killinger | 604/413 |
| 3,987,791 | 10/1976 | Chittenden et al. | 604/413 |
| 4,233,973 | 10/1980 | Shukla | 604/84 |
| 4,432,755 | 2/1984 | Pearson | 604/413 |
| 4,465,471 | 8/1984 | Harris et al. | 604/85 |
| 4,534,758 | 8/1985 | Akers | 604/247 |

Primary Examiner—C. Fred Rosenbaum
Assistant Examiner—Karen Kaechele
Attorney, Agent, or Firm—Barnes & Thornburg

[57] ABSTRACT

An apparatus for connecting a vial into the delivery tube of an intravenous administration set, the set including a container of fluid connected to one end of a delivery tube with the other end of the delivery tube adapted for insertion into the patient. The apparatus includes a penetrating spike penetrating an end of the vial which provides two pathways into the interior of the vial with two sections of the delivery tube connected to the two pathways of the penetrating spike. The apparatus also includes a frame for maintaining the two sections of the delivery tube adjacent to each other and clamp for releasably closing the adjacent sections of the delivery tube to temporarily prevent flow of fluid through the penetrating spike.

9 Claims, 3 Drawing Figures

VACUUM VIAL INFUSION SYSTEM

This invention relates generally to systems for intravenously administering medicine to a patient and more particularly to a system for reconstituting a drug from a dried state to a liquid state while the drug is still within the conventional drug-containing vial and thereafter administering the reconstituted drug by means of a primary intravenous administration set into which the drug vial is serially connected by means of an adaptor.

Conventional medical treatment frequently requires the intravenous administration of fluids and medicated solutions. Such fluids can include saline and dextrose solutions as well as other solutions to correct imbalances in body chemistry and medication solutions to treat disease. Many such solutions are frequently available in commercial aseptic solution containers that are adapted to be punctured at one end and to be hung by the other end so that their liquid contents may be removed and infused in a vein of a patient by means of primary intravenous administration set, commonly referred to as an I.V. set. In effecting such treatment, the closure of the solution container is punctured by a spike on the upper end of the delivery tube or conduit of the I.V. set so as to conduct the liquid material from the solution container to a hypodermic needle or butterfly situated for injection into a vein of the patient.

Such I.V. sets generally also include a transparent drip chamber which includes the conduit-forming spike at the upper end which is intended to perforate and enter the solution container. The transparent drip chamber is generally employed as a means to measure the administration rate of the fluid to the patient, the rate typically being measured in drops per minute. A transparent flexible plastic tube is generally attached to the lower end of the drip chamber and a regulating clamp is provided as means to control the flow of liquid through the passageway of the plastic tube. One or more Y injection sites can be provided to attach other medicament dispensers. The I.V. set may also include a pump to control the rate of delivery of fluid to the patient as well as a particle filter and air eliminator to insure that no air or small particles of medicine or foreign matter enter into the vein of the patient. Generally the use of conventional I.V. sets requires aseptic techniques and the I.V. set is protected against contamination during handling at the point of attachments by appropriate protective end caps and the like.

Certain of the medicines which are desirably administered to a patient by an intravenous administration set are manufactured and packaged in dry form due principally to their instability in liquid solution. The drug in dry form is typically commercially delivered in a standard glass vial containing up to two grams of the medication. The glass vial is closed with a rubber stopper and crimped aluminum seal, the aluminum seal usually having a flip off plastic cover intended to keep the top of the rubber stopper clean and to provide a means of tamper evidence. The glass vial itself is generally sized to accommodate about 10 to 15 cubic centimeters.

To reconstitute the dried drug compound, the general practice in the prior art was to remove the plastic seal exposing the rubber stopper and, after wiping the stopper with an antiseptic wipe, adding five to ten cc's of sterile water diluent by inserting the needle of a syringe through the rubber stopper and depositing the contents of the syringe into the vial. One would then shake the vial to make sure the drug compound within the vial was fully dissolved or suspended in the diluent to form a reconstituted drug solution. This reconstituted solution was then withdrawn from the vial by means of a syringe, the needle of which was again inserted through the rubber stopper. The reconstituted solution was then typically injected into a plastic or glass container which had been previously filled with 50 or 100 cc's of a compatible I.V. diluent such as sterile water with a small percentage of dextrose of sodium chloride added. This container containing the fully diluted drug was then attached to the I.V. administration set with a separate drip chamber usually at a Y site and hung slightly above the primary I.V. source container.

If the reconstituted drug was not intended for immediate use, it was generally stored under a refrigerated condition until such time as the patient was ready for its administration. Once a drug compound has been reconstituted, however, a degradation of the compound begins. Refrigeration will slow this process but it is generally accepted practice to administer the reconstituted drug within a few hours, or at most one or two days so as to prevent any substantial degradation of the drug compound. Due to many influences such as patient reactions to the drug, patient recoveries, and the like, substantial percentages of the reconstitued drugs are not used within the acceptable time limits and must be discarded. Some of the drug compound itself is lost during the reconstitution steps as it is difficult to remove all of the reconstituted solution from the original drug containing vial by means of the syringe and needle. For this reason, the general commercial practice mandated by the *United States Pharmacopeia* is to over fill the vials to provide for vial and syringe protection, commonly amounting to approximately a 7% overfill. Other losses of the drug occur as the fully reconstituted container empties into the Y site through a drip chamber, some of the drug remains undelivered in the drip chamber. All of these losses tend to increase the cost of drugs to the ultimate purchaser, whether that be the patient or an insurance company.

Systems have been developed for the administration of medicines which are typically packaged in standard small glass vials which include a valve adaptor to a primary intravenous administration set which adaptor serially connects the drug containing vial directly to the primary delivery tube of the I.V. set in such a fashion as to permit administration of the contents of the vial to the patient. One such system is disclosed in application Ser. No. 512,268 filed July 5, 1983. The valve adaptor includes means operable to a first and a second position providing for the dilution of the contents of the vial in the first position with liquid from the primary I.V. solution container, and after the drug is resuspended within the vial, the valve means permits delivery of the diluted contents of the vial in the second position directly to the primary I.V. passageway. This use of the conventional small drug containing vial as the mixing and delivery chamber after connection with the primary I.V. set eliminates any separate reconstitution in a hospital pharmacy, and the consequent need for refrigeration, eliminates the need for separate delivery containers and secondary I.V. sets, and reduces storage space requirements. Such systems have been found to deliver all of the drug in the vial, thereby substantially eliminating the need for the 7% over fill typically practiced in the industry.

The valve adaptor employed in the previously described system requires some manipulation by the nurse or other person administering the drug. This manipulation is subject to error. The valve adaptor generally includes a number of parts which must be movable with respect to each other to achieve the valving action. These parts must be manufactured to very close tolerances to achieve a satisfactorily low risk of drug contamination and minimization of exposure of hospital personnel to the drug compound. Consequently, the cost of manufacture of the valve adaptor tends to be undesirably high.

The present invention provides a system for the administration of medicines through a serial connection with the primary delivery tube of an I.V. set which avoids the use of hand-manipulated valves. A partial vacuum is provided in the drug-containing vial which acts to draw liquid from the I.V. solution container at the time the vial is attached to the serial connector. As flow of I.V. solution through the administration set is re-established, the drug vial is continuously flushed with the I.V. solution thus delivering the drug to the patient. The serial connector is preferably constructed to include a means for releasably closing the delivery tube to permit ease of introduction of the drug vial into the primary delivery tube without modification of the drip rate which can be preset with a separate conventional regulating clamp. The serial connector is also preferably provided with a short cap through which the I.V. solution can flow prior to the attachment of the drug-containing vial. The connector can also include means for restricting fluid flow so as to prevent fluid from being drawn from the patient. The serial connector is configured with offset inlet and outlet lines such that the drug-containing vial is held in an inverted position by the weight of the depending primary delivery tube.

Additional features and advantages of the invention will become apparent to those skilled in the art upon consideration of the following detailed description of prefered embodiments exemplifying the best mode of carrying out the invention as presently preceived. The detailed description particularly refers to the accompanying figures in which.

Figure 1:
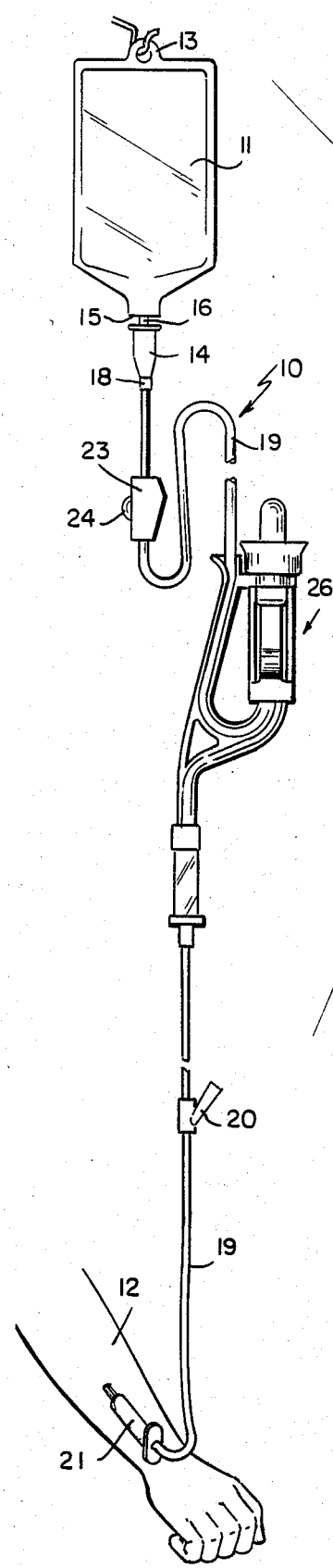
FIG. 1 is a schematic illustration of a primary I.V. administration set including a serial connector of the present invention.
Figure 2:
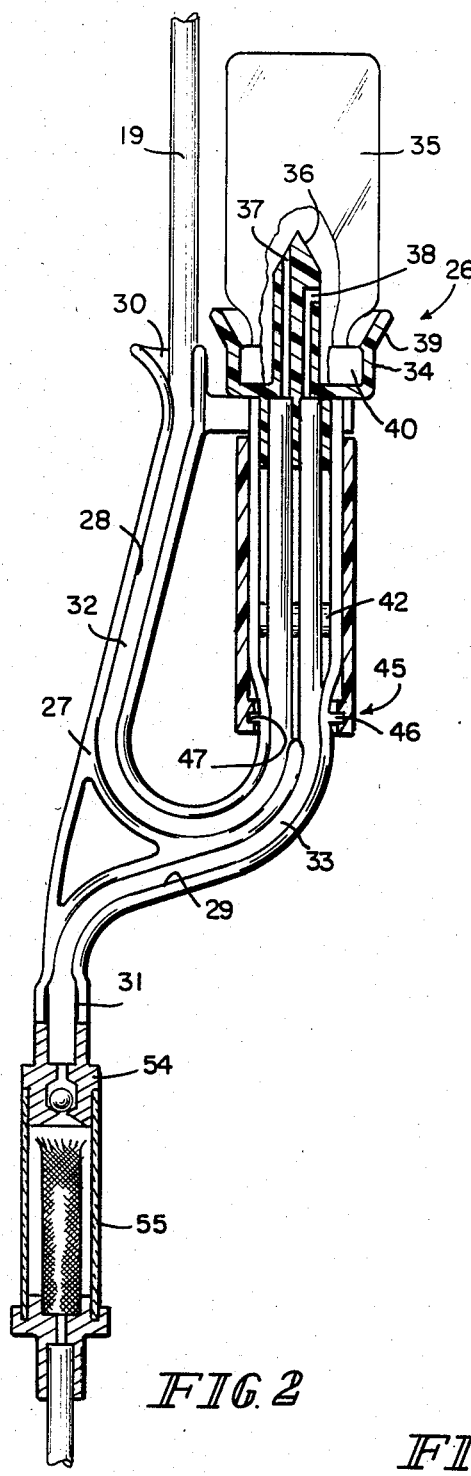
FIG. 2 is a detail view partially in section showing the addition of a drug containing vial to the serial connector.
Figure 3:
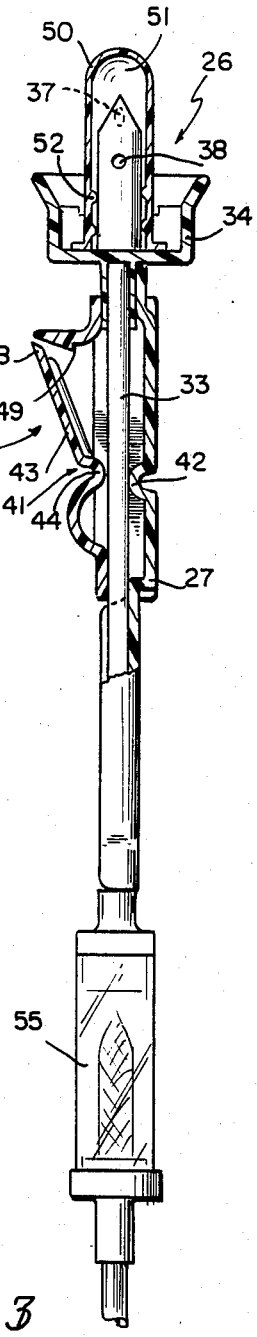
FIG. 3 is a detail view from the right side of FIG. 2 partially in section showing the serial connector without a vial.

The system 10 of this invention is shown in FIGS. 1 through 3 to include a container 11 containing a source of liquid for delivery to a patient 12. The source of liquid 11 can be any conventionally employed source such as the type manufactured by Travenol Laboratories, Inc., of Deerfield, Ill., 60015, and sold under the registered trademark VIAFLEX as an I.V. fluid container. Glass bottles can also serve as a fluid reservoir. Generally such containers are transparent and include means 13 for suspending the container above the patient. A drip chamber 14 generally included with a conventional I.V. set includes a spike 16 adapted to perforate and enter closure 15 on the lower end of container 11. Prior to its insertion into the closure 15, the spike 16 is protected by cover so as to prevent contamination of the spike and conduit within the spike. The drip chamber 14 is formed from a flexible transparent material, typically plastic to permit visual monitoring of the rate at which liquid is being administered to the patient. The lower end 18 of the drip chamber is connected to a conduit 19 typically formed of a transparent flexible plastic tube intended to carry the liquid from the drip chamber 14 to the patient. One or more Y injection sites 20 can be provided for the connection of additional sources of fluids and medicines to the system. The Y injection sites provide a sterile access to the passageway within the tubing 19. Each Y injection site 20 is closed by a standard rubber stopper adapted to receive a hypodermic needle or the like in a sterile fashion. A luer needle adaptor 21 is provided at the lower end of the I.V. system. The adaptor permits the connection of the lower end of the I.V. tubing to a hypodermic needle inserted in a vein of the patient 12. The lower end of the needle adaptor 21 is also typically protected by a cover until the system is ready for use. A clamp 23 is provided at some point along the tubing 19 for regulating the flow through the tubing. The clamp 23 includes a serrated roller 24 which engages the outer surface of the flexible plastic tube 19 to pinch the tube to a desired degree thereby imposing a restriction upon the size of the passageway within the tubing and hence controlling the rate at which liquid from the container 12 passes through the tubing 19. All of the components previously mentioned are conventionally available and are distributed by IVAC Corporation of San Diego, Calif. 92121.

In accordance with the present invention, a serial connector 26 is included in the previously described portions of the primary I.V. administration set. The serial connector 26 includes a frame 27 having an upper channel 28 and a lower channel 29, each of which are adapted to receive a segment of the delivery tube 19. The upper end 30 of upper channel 28 is laterally offset from the lower end 31 of lower channel 29. This lateral offset coupled with the weight of the primary tube 19 and other apparatus positioned below the serial connector 26 imparts a torque on the frame 27 as will be later discussed.

The delivery tube 19 can be considered to be divided into an upper portion 32 which is received in the upper channel 28 and a middle portion 33 which is received in the lower channel 29. The two portions 32 and 33 of the primary delivery tube 19 are held in an adjacent and substantially parallel relationship and terminate at penetrating means 34 which is provided for penetrating an end of a drug-containing vial 35. The penetrating means 34 generally comprises a central spike 36 including two channels 37 and 38 providing pathways to the interior of the vial. The two sections 32 and 33 of the primary delivery tube 19 are connected to the two pathways 37 and 38 of the penetrating means. The penetrating means also includes a peripheral, upstanding flange 39 adapted to receive and hold the outer lip 40 of the penetrable end of the drug-containing vial 35. The previously mentioned torque provided by the offset of the upper end 30 from the lower end 31 frame together with the depending weight of the primary I.V. set below the serial connector 26 acts to maintain the drug-containing vial 35 in an inverted position when connected to the penetrating means 34.

The serial connector also includes a clamping means 41 to clamp both tubes 32, and 33, illustrated best in FIG. 3. The clamping means is in part provided by a ridge or offset 42 in the wall of frame 27. The ridge or offset 42 is situated opposite a movable element 43 which also includes a ridge or offset 44. The movable element 43 is pivotally supported to the frame by a pivot means 45 shown in FIG. 2 to comprise a pair of outwardly-extending stub axles 46 integrally formed with the frame 27 being received within slots or dimples 47 on the inner surface of movable element 43. As a force is imparted in the direction F, as illustrated in FIG. 3, the movable member 43 pivots about the pivot means 45 to reduce the distance between protrusions 42 and 44, thereby pinching or clamping the adjacent portions 32 and 33 of the primary tube 19 which prevents the flow of fluid through the tubes and, hence, through the penetrating means 34. The application of force F causes the displacement of the upper end 48 of the clamping means so as to engage a serrated portion 49 of the frame which acts to lock the movable portion 43 in a fixed, clamped position with respect to the frame 27. The movable portion and, hence, the clamping function can be released by upwardly displacing the serrated portion 49 of the frame.

As shown in FIG. 3, the serial connector 26 is originally supplied with a cap 50 which includes a small space 51 sufficient to permit the flow of the fluid from pathway 37 to pathway 38 even in the absence of a vial 35. The cap 50 includes ridges or other means 52 for hermetically sealing the cap to the spike 36 of the penetrating means 34. In use, the serial connector 26 would preferably be supplied in a sterile condition with the cap 50 in place as illustrated in FIG. 3.

The serial connector can also include a check valve 54 such as that illustrated in FIG. 2. Alternatively, a check valve such as that illustrated in U.S. Pat. No. 4,141,379 can be employed. The purpose of the check valve is to insure that the fluid flow is downward through the system, as illustrated in the Figs., from the source of fluid 11 to the patient 21 and that no fluid is drawn upward through the system from the portion of the I.V. situated below the serial connector 26.

The serial connector can also include an air and particle filtering means 55. Alternatively, a conventional particle/air filter such as model 2C0251 available from Travenol Laboratories can be included. In either event, the filter means 55 is intended to prevent air or particles of medicine or foreign matter from entering the lower portion of the I.V. set. The filter means 55 also functions to prevent or restrict reverse flow through the I.V. set thus rendering the check valve 54 optional.

The serial connector means 26 illustrated in FIGS. 1 through 3, has particular utility when combined with a vial 35 containing a medicine under a partial vacuum, that is, under less than atmospheric pressure. To employ the illustrated connector in such a combination, the I.V. administration set illustrated in FIG. 1 is purged of air and connected to the patient 12 and the delivery rate of the fluid from source 11 is established by appropriate manipulation of the serrated roller 24 of regulating clamp 23. The clamping means 41 is then engaged so as to clamp the adjacent sections 32 and 33 of the delivery tube 19. The cap 50 is then removed from the spike 36 of the penetrating means 34. A vial containing medicine under less than atmospheric pressure is situated at the top of the penetrating means and forced downwardly thereover until it is engaged by the retaining ring 39 as shown in FIG. 2. This causes the penetrating spike 36 to enter into the interior of the drug-containing vial 35 to provide the two pathways 37 and 38 with access to the interior of the vial 35.

The clamping means 41 is then released from its clamped position. As it is released, the partial vacuum within the vial 35 causes fluid to be quickly drawn down through the upper tubular member 32 into the vial to mix with the drug contained therein. The check valve 54 acts to prevent any significant portion of fluid from being drawn upwardly through the tubing portion 43. The amount of fluid drawn within the drug-containing vial 35 can be determined in part by the extent to which the pressure within the vial has been reduced. Early experiments have shown that approximately a one-half atmosphere pressure is sufficient to impel enough fluid into the vial to permit the full reconstitution or solution of the drug within the vial 35.

As soon as the pressure within drug vial 35 achieves atmospheric levels, the drip rate from container 11 down through the primary delivery tube 19 is re-established at the rate initially set since no significant change in pathway has resulted from the replacement of cap 50 with drug-containing vial 35. The continued delivery of the liquid from container 11 acts to dilute the medicine within vial 35 and deliver the diluted medicine to the patient through the primary tubing 19, needle adaptor 21 and associated hypodermic needle, etc. As the delivery of the contents of container 11 continues, the drug within the vial 35 is substantially totally delivered to the patient and thereafter the vial 35 may be viewed as merely a portion of the delivery tubing 19.

The drug-containing vials can easily be prepared so as to contain less than atmospheric pressure by subjecting a conventional drug-containing vial to a vacuum condition. A particularly useful method of achieving this end can be achieved by modifying only slightly the conventional freeze-drying packaging process. As in the conventional practice, a solution of medicine or drug is placed within the vial. The vial is then frozen in a freeze dryer under a reduced atmospheric pressure so as to draw the undesired water from the drug. The conventional process is modified by merely sealing the vial while still within the freeze dryer at a less than atmospheric pressure. Of course, some drugs are not manufactured under freeze-drying conditions and thus other methods must be used in order to achieve a partially-evacuated drug-containing vial. Alternative methods can include the use of mechanical pumps or the like.

One particularly advantageous method for achieving a reduced absolute pressure within the vial involves the use of functionally inert gases such as helium, carbon dioxide, Freons, or the like, which have low concentrations in the atmosphere and which are capable of penetrating the material forming the stopper of the vial, typically rubber. In accordance with this method, after the medicine or drug is placed within the vial, the remaining volume of the vial is flooded with the selective gas and the vial stopper promptly inserted. The vial is then subjected to conventional atmospheric conditions during which time the inert gas selectively migrates through the material forming the stopper and diffuses into the atmosphere due to the large partial pressure differential existing between the inside and outside of the vial. Very little reverse transportation of gas from the atmosphere occurs thus resulting in a lowering in the absolute pressure within the vial. After the inside pressure has been decreased to the desired amount, the vial can be overcapped with a gas impermeable layer such as a metal foil to help maintain the pressure differential.

Although the invention has been described in detail with reference to the illustrated preferred embodiment, other variations and modifications may exist within the scope and spirit of the invention as described and as defined in the following claims:

We claim:

1. In an intravenous administration set comprising a container containing a fluid, a delivery tube connected to the container for dispensing fluid therefrom, injection means for connecting the delivery tube to a patient, a drip chamber situated in the delivery tube for permitting the determination of the administration rate of the fluid, and control means for controlling the administration rate of the fluid, the improvement comprising: a vial containing a medicine under a partial vacuum, penetrating means penetrating an end of the vial to provide two pathways to the interior of the vial, two adjacent sections of the delivery tube being arranged contiguous to each other and connected to the two pathways of the penetrating means, fluid flow restricting means situated in the delivery tube between the injection means and the penetrating means for permitting fluid flow into the vial only from said container, and means embracing said adjacent sections of the delivery tube for releasably closing both pathways to the interior of the vial to temporarily prevent flow of fluid through the penetrating means.

2. The improvement of claim 1 wherein the means for releasably closing to the two pathways comprises a clamp for simultaneously constricting the two sections of the delivery tube.

3. The improvement of claim 1 wherein the fluid flow restricting means comprises a particle/air filter.

4. The improvement of claim 3 wherein the fluid flow restricting means further comprises a check valve.

5. Apparatus for connecting a vial in the delivery tube of an intravenous administration set, the set including a source of fluid connected to one end of the delivery tube, the other end of which is adapted to be inserted in a patient, the apparatus comprising: penetrating means penetrating an end of the vial to provide two pathways to the interior of the vial, two sections of the delivey tube connected to the two pathways of the penetrating means, frame means for maintaining the two sections of the delivery tube adjacent to each other, and a clamp connected to the frame means and embracing both of said two sections for releasably clamping the adjacent sections of the delivery tube to temporarily prevent flow of fluid through the penetrating means.

6. The apparatus of claim 5 further comprising filter means for filtering particulate matter and air from the delivery tube.

7. The apparatus of claim 5 further comprising flow restricting means for preventing fluid flow up the delivery tube from the patient to the vial.

8. Apparatus for connecting a vial in the delivery tube of an intravenous administration set, the set including a source of fluid connected to one end of the delivery tube, the other end of which is adapted to be inserted in a patient, the apparatus comprising: penetrating means penetrating an end of the vial to provide two pathways to the interior of the vial, two sections of the delivery tube connected to the two pathways of the penetrating means, frame means for maintaining the two sections of the delivery tube adjacent to each other, and clamping means for releasably clamping the adjacent sections of the delivery tube to temporarily prevent flow of fluid through the penetrating means, the clamping means including pivot means connecting the clamping means to the frame means.

9. Apparatus for connecting a vial in the delivery tube of an intravenous administration set, the set including a source of fluid connected to one end of the delivey tube, the other end of which is adapted to be inserted in a patient, the apparatus comprising: penetrating means penetrating an end of the vial to provide two pathways to the interior of the vial, two sections of the delivery tube connected to the two pathways of the penetrating means, a frame for receiving the two sections of the delivery tube, the tubes positioned by the frame to have divergent end portions offset from each other to maintain the vial in an inverted position and intermediate portions contiguous to each other for maintaining the two sections of the delivery tube adjacent to each other, the frame comprising clamping means for releasably clamping the adjacent sections of the delivery tube to temporarily prevent flow of fluid through the penetrating means.

* * * * *